US012618012B2

(12) United States Patent
Fujii et al.

(10) Patent No.: US 12,618,012 B2
(45) Date of Patent: May 5, 2026

(54) METHOD FOR PRODUCING HYDROCARBON

(71) Applicant: NATIONAL INSTITUTE OF ADVANCED INDUSTRIAL SCIENCE AND TECHNOLOGY, Tokyo (JP)

(72) Inventors: Takashi Fujii, Ibaraki (JP); Masateru Nishioka, Miyagi (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 547 days.

(21) Appl. No.: 18/031,476

(22) PCT Filed: Sep. 17, 2021

(86) PCT No.: PCT/JP2021/034373
§ 371 (c)(1),
(2) Date: Apr. 12, 2023

(87) PCT Pub. No.: WO2022/080088
PCT Pub. Date: Apr. 21, 2022

(65) Prior Publication Data
US 2023/0382822 A1      Nov. 30, 2023

(30) Foreign Application Priority Data

Oct. 14, 2020      (JP) ................................. 2020-173427

(51) Int. Cl.
*C10G 2/00*           (2006.01)
*B01J 21/04*          (2006.01)
(Continued)

(52) U.S. Cl.
CPC ................ *C10G 2/50* (2013.01); *B01J 21/04* (2013.01); *B01J 23/755* (2013.01); *B01J 35/19* (2024.01);
(Continued)

(58) Field of Classification Search
None
See application file for complete search history.

(56) References Cited

U.S. PATENT DOCUMENTS

2019/0010791 A1*    1/2019   Baxter ................ E21B 43/2605

FOREIGN PATENT DOCUMENTS

JP          7-80309 A        3/1995
JP          2000-104078 A    4/2000
(Continued)

OTHER PUBLICATIONS

Budisa, N. et al. "Supercritical Carbon Dioxide and Its Potential as a Life-Sustaining Solvent in a Planetary Environment" Life 2014, 4, 331-340; doi: 10.3390/life4030331 (Year: 2014).*
(Continued)

*Primary Examiner* — Medhanit W Bahta
(74) *Attorney, Agent, or Firm* — Birch, Stewart, Kolasch & Birch, LLP

(57)          ABSTRACT

$CO_2$ introduced into the ground reacts with water in the moisture present in the surroundings to convert to hydrocarbon, suppressing leakage of $CO_2$ above ground. The method for producing hydrocarbon has an introduction step for introducing $CO_2$ into a storage site in the ground where moisture and a catalytic metal are present, the pressure is 5 MPa or higher, and the temperature is 40° C. or higher, to bring the $CO_2$ into a subcritical state or a supercritical state, and a synthesis step for reacting the water in the moisture with the subcritical or supercritical $CO_2$ in the storage site to synthesize hydrocarbon. The storage site is preferably a site
(Continued)

from 800 m to 1200 m below ground. The pressure of the storage site is preferably 8 MPa or higher.

6 Claims, 4 Drawing Sheets

(51) Int. Cl.

| | | |
|---|---|---|
| *B01J 23/755* | (2006.01) |
| *B01J 35/00* | (2024.01) |
| *B01J 35/30* | (2024.01) |
| *B01J 35/45* | (2024.01) |
| *B01J 35/50* | (2024.01) |
| *B01J 37/02* | (2006.01) |
| *B01J 37/08* | (2006.01) |
| *C07C 1/12* | (2006.01) |

(52) U.S. Cl.
CPC ......... *B01J 35/397* (2024.01); *B01J 37/0201* (2013.01); *B01J 37/088* (2013.01); *C07C 1/12* (2013.01); *C10G 2/332* (2013.01); *C10G 2/333* (2013.01); *B01J 35/45* (2024.01); *B01J 35/50* (2024.01); *B01J 2235/00* (2024.01); *B01J 2235/10* (2024.01); *Y02P 20/54* (2015.11)

(56) References Cited

FOREIGN PATENT DOCUMENTS

| | | |
|---|---|---|
| JP | 2010-119962 A | 6/2010 |
| JP | 2010-201330 A | 9/2010 |
| JP | 2015-77575 A | 4/2015 |

OTHER PUBLICATIONS

Benson, S. et al. "Underground Geological Storage" Chapter 5, 2005, Cambridge University Press (Year: 2005).*
International Search Report, issued in PCT/JP2021/034373, PCT/ISA/210, dated Nov. 30, 2021.
Written Opinion of the International Searching Authority, issued in PCT/JP2021/034373, PCT/ISA/237, dated Nov. 30, 2021.
Australian Office Action for Australian Application No. 2021361513, dated May 7, 2024.

* cited by examiner

Introduce supercritical CO₂ water  catalyst

Retention time (min)

Retention time (min)

Retention time (min)

Retention time (min)

Retention time (min)

METHOD FOR PRODUCING HYDROCARBON

TECHNICAL FIELD

The present application relates to a method in which $CO_2$ stored in the ground is converted to a solid or liquid hydrocarbon, thereby reducing $CO_2$ above ground and obtaining a valuable resource.

BACKGROUND ART

A system for storing and sequestrating $CO_2$ is known in which $CO_2$ is dissolved in a solvent and injected into an underground aquifer by pressure (Patent literature 1). According to the system in Patent literature 1, $CO_2$-dissolved water can be stored in the ground at a concentration close to the saturation concentration. However, if $CO_2$-dissolved water is stored underground for a long period of time, there is a risk of $CO_2$ leaking to the ground surface. The emergence of a technology to suppress the leakage of $CO_2$ stored underground to the ground surface has been desired.

PRIOR ART LITERATURE

Patent Literature

Patent literature 1: JP 2010-201330 A

SUMMARY OF INVENTION

Problem to be Solved by the Invention

The objective of the present application is to provide a method for suppressing $CO_2$ leakage to the ground surface by synthesizing a hydrocarbon from water and $CO_2$ underground.

Means for Solving the Problem

A method for producing a hydrocarbon in one aspect of the present application comprises: an introduction step in which $CO_2$ is brought into a subcritical or supercritical state by introducing $CO_2$ into an underground storage site where moisture and a catalytic metal are present, the pressure is 5 MPa or higher, and the temperature is 40° C. or higher; and a synthesis step in which water in the moisture and $CO_2$ in the subcritical or supercritical state are allowed to react at the storage site to synthesize the hydrocarbon. A method for producing a hydrocarbon in another aspect of this application comprises: an introduction step in which $CO_2$ is brought into a subcritical or supercritical state by introducing catalytic particles comprising a catalytic metal and $CO_2$ into an underground storage site where moisture is present, the pressure is 5 MPa or higher, and the temperature is 40° C. or higher; and a synthesis step in which water in the moisture and $CO_2$ in the supercritical state are allowed to react at the storage site to synthesize the hydrocarbon.

Effects of Invention

According to the present application, $CO_2$ introduced into the ground reacts with water present in the surrounding moisture to produces a hydrocarbon, and therefore $CO_2$ is less likely to leak to the ground surface. In addition, according to the present application, the hydrocarbon produced underground can be extracted and used as a valuable resource.

MODE FOR CARRYING OUT THE INVENTION

Figure 1:
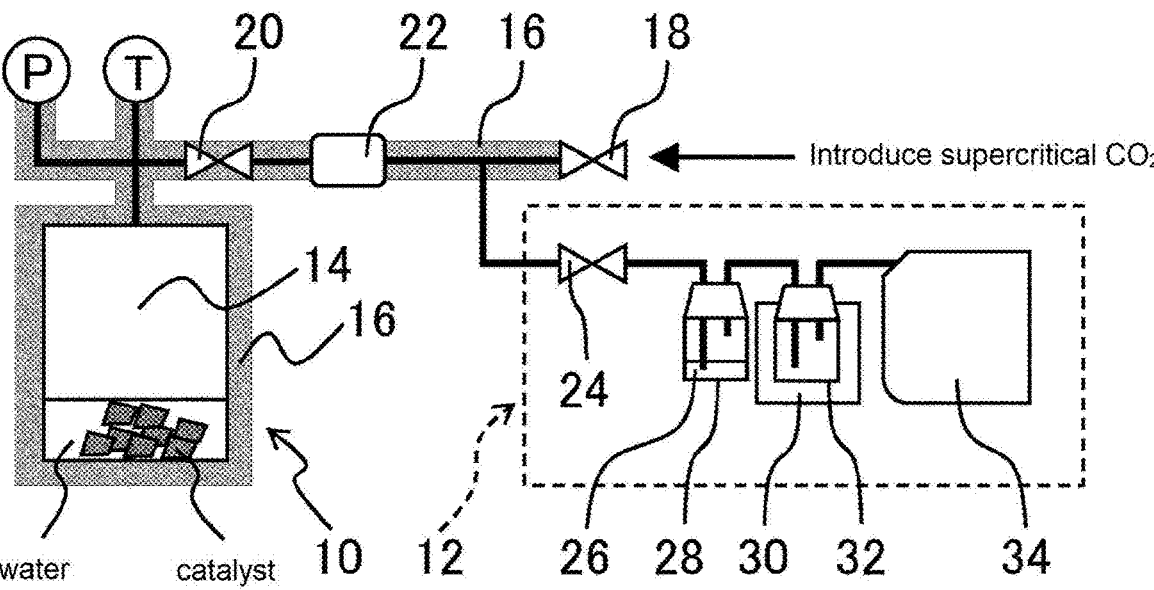
FIG. 1 A schematic diagram of a reactor and a collection unit used in Examples.

A method for producing a hydrocarbon according to an embodiment of the present application comprises an introduction step and a synthesis step. In the introduction step, $CO_2$ is brought into a subcritical or supercritical state by introducing $CO_2$ into an underground storage site where moisture and a catalytic metal are present, the pressure is 5 MPa or higher, and the temperature is 40° C. or higher. In other words, in the introduction step, $CO_2$ is introduced into an underground storage site where water and a catalytic metal are present and $CO_2$ becomes subcritical or supercritical. $CO_2$ can be introduced, for example, by connecting the ground surface and the storage site with a pipe, which can be used to inject $CO_2$ by pressure.

This storage site may be, for example, a cleavage, fissure, or pore in a soil or rock formation. Moisture may be rainwater or surface water that has percolated from the ground surface into the subsurface and been stored in cleavages, fissures, or pores in the soil or rock formations, or it may be water of crystallization, such as the water component of a metal salt hydrate present in the ground. Catalytic metals are present as mineral compositions in soil or rock formations, or are attached to cleavages, fissures, or pores in soil or rock formations. From the perspective of storing $CO_2$ at the storage site, $CO_2$ introduced into the ground is preferably a gas or liquid. The storage site where $CO_2$ becomes subcritical or supercritical is, for example, at a temperature of 40° C. or higher and a pressure of 8 MPa or higher.

In Japan, moisture is generally present and metals that can serve as catalysts are often present at depths between 800 m and 1,200 m below the ground surface. In addition, the temperature is often between 40° C. and 50° C., and the pressure is often between 8 MPa and 12 MPa at depths between 800 m and 1,200 m below the ground surface. Therefore, any point between 800 m and 1,200 m below the ground surface can be used as the storage site without any concern for the presence of moisture and catalytic metals, as well as the temperature and pressure. When $CO_2$ is introduced into such a storage site, $CO_2$ becomes subcritical or supercritical, thereby creating an environment for the synthesis step.

In the synthesis step, water in the moisture and $CO_2$ in the subcritical or supercritical state are allowed to react at the storage site to synthesize a hydrocarbon. This synthesis step proceeds by leaving them as they are, i.e., with the passage of time, after the introduction step. The time of synthesis may range from a few years to several hundred years. Thus, $CO_2$ introduced into the ground is converted to a hydrocarbon, which is less likely to leak to the ground surface. Since the hydrocarbon obtained in the synthesis step is either liquid or solid, there is little possibility of leakage to the ground surface. Moreover, if the hydrocarbon is removed from the ground, it can be used as a valuable resource. Therefore, the method for producing a hydrocarbon according to this embodiment may further include a collection step in which the hydrocarbon is collected from the storage site to the ground surface.

The catalytic metal is preferably a metal that allows the Fischer-Tropsch reaction to proceed. The Fischer-Tropsch reaction is a reaction of synthesizing a hydrocarbon from $H_2$ and CO using a catalyst. The present inventors have found that, under given conditions, a hydrocarbon can be obtained even if $CO_2$ is used instead of CO. Therefore, according to the method for producing a hydrocarbon of the present embodiment, $CO_2$ emitted from various industries and considered to be a cause of global warming can be reduced. Examples of the catalytic metal that allows the Fischer-Tropsch reaction to proceed include Ni, Fe, Co, Pd, Cu, Ag, and Zn. The catalytic metal is preferably one or more among Ni, Fe, Co, and Pd. This is because the hydrocarbon can be obtained efficiently. The catalytic metal in the form of a metal or metal salt may be supported on a support such as a ceramic or activated carbon.

In an embodiment which uses a catalytic metal that allows the Fischer-Tropsch reaction to proceed, water is expected to serve as the $H_2$ source and subcritical or supercritical $CO_2$ is expected to serve as the CO source. Specifically, in the presence of a catalytic metal that allows the Fischer-Tropsch reaction to proceed, the reaction of water with $CO_2$ in a subcritical or supercritical state provides $H_2$ from water and CO from $CO_2$, and the Fischer-Tropsch reaction produces a hydrocarbon from $H_2$ and CO.

In the introduction step of the present embodiment, $CO_2$ is brought into a subcritical or supercritical state by introducing $CO_2$ into an underground storage site where moisture and a catalytic metal are present, the pressure is 5 MPa or higher, and the temperature is 40° C. or higher. Alternatively, in the introduction process, $CO_2$ may be brought into a subcritical or supercritical state by introducing catalytic particles comprising a catalytic metal and $CO_2$ (for example, by simultaneously injecting the catalytic particles and $CO_2$ by pressure) into an underground storage site where moisture is present, the pressure is 5 MPa or higher, and the temperature is 40° C. or higher. Alternatively, $CO_2$ may be brought into a subcritical or supercritical state by introducing catalytic particles comprising a catalytic metal and $CO_2$ into an underground storage site where moisture and a catalytic metal are present, the pressure is 5 MPa or higher, and the temperature is 40° C. or higher.

It is desirable that the catalytic particles have a highly fluid shape so that they do not place a burden on the introduction equipment including a piping provided between the ground and the storage site or a pump for transferring the fluid in the piping to the storage site, and do not interfere with the diffusion of the catalytic particles into a cleavage, fissure or pore in a soil or rock formation at and around the storage site. A highly fluid shape is preferably a spherical shape, a shape with few protrusions, or a small particle shape. This is because introduction of the catalytic particles comprising a catalytic metal, together with $CO_2$, into the storage site can promote the reaction between water and subcritical or supercritical $CO_2$ at the storage site.

These catalytic particles are preferably core-shell catalytic nanoparticles each having a core which is a nanoparticle support, and a shell which is the catalytic metal, to give a highly fluid shape. This is because catalytic particles having a smaller size allow them to be delivered to the storage site through the tube connecting the ground and the storage site. The particle size of the nanoparticle support is, for example, 10 nm to 500 nm. Examples of the nanoparticle support include silica nanoparticles and alumina nanoparticles. Such core-shell catalytic nanoparticles can be prepared, for example, according to the method described in Japanese Patent No. 6303499.

Fly ash, which is considered to be highly fluid, can also be used as the catalytic particles to be introduced into the storage site. Fly ash is a byproduct from coal-fired power plants, which is generated when an inorganic material contained in raw coal excavated from the ground is melted during the combustion process. Moreover, the shape of fly ash is spherical. In addition, fly ash may contain a catalytic metal such as Fe or Ni, depending on the coal-producing areas. In order to improve the catalytic performance of fly ash, it is also useful to zeolitize the surface thereof. Zeolitization of the surface of fly ash can be performed by the method described, for example, in "Physical Property of Potassium-chabazite Obtained by Alkali Hydrothermal Synthesis from Coal Fly Ash" (Journal "Shigen to Sozai" (Journal of the Mining and Materials Processing Institute of Japan), Vol. 119, p. 125-129, (2003)).

EXAMPLES

FIG. 1 schematically shows a reactor 10 as a model of a storage site, and a collection unit 12 for collecting the hydrocarbon produced in the reactor 10. The reactor 10 was provided with a reaction vessel 14, a heater 16 installed around the reaction vessel 14, and a pressure gauge P and a thermometer T connected to the reaction vessel 14. A hydrocarbon was synthesized from water and subcritical or supercritical $CO_2$ in the presence of a catalytic metal in the reaction vessel 14. The heater 16 maintained a predetermined temperature, for example, not lower than 40° C. and not higher than 50° C., inside the reaction vessel 14. The reaction vessel 14 was connected to piping and a valve 18 for introducing subcritical or supercritical $CO_2$.

The heater 16 was also installed around the piping extending from each of the valve 18, pressure gauge P, and thermometer T to the reaction vessel 14. A valve 20 for isolating the reactor 10 and a filter 22 for preventing solids generated in the reaction vessel 14 from flowing into the collection unit 12 were provided between the valve 18 and the reaction vessel 14. There was no heater 16 around the filter 22, and the temperature around the filter 22 was about 15° C. in the present examples. The collection unit 12 was provided with a valve 24 for collecting the synthesized hydrocarbon, a trap 28 containing deuterated chloroform 26, a trap 32 surrounded by cooling means 30, and a gas sampling bag 34.

1. Synthesis of Hydrocarbon

Example 1

9.0 g of dried porous γ-alumina pellets (manufactured by FUJIFILM Wako Pure Chemical Corporation) were immersed in 24 mL of 10 wt % aqueous nickel nitrate solution prepared with nickel (II) nitrate hexahydrate (manufactured by FUJIFILM Wako Pure Chemical Corporation). The pellets were impregnated with nickel nitrite and dried in a rotary evaporator. The resulting nickel nitrate-impregnated $\gamma$-alumina pellets were calcined in air at 800° C. for 3 hours, and further reduced in a hydrogen atmosphere at 550° C. for 3 hours to prepare catalytic particles having catalytic metal Ni supported on the substrate $\gamma$-Al$_2$O$_3$. Note that Ni is a metal that promotes the Fischer-Tropsch reaction. 4.0 g of these catalytic particles and 2 mL of pure water were placed in a stainless steel reaction vessel 14 with a volume of 30 mL.

With the valve 24 closed, supercritical CO$_2$ was introduced into the reaction vessel 14 through the valve 18. The valve 20 was closed and the temperature and pressure in the reaction vessel 14 were kept at 40° C. and 8.8 MPa, respectively, to allow water and supercritical CO$_2$ to react for 5 days. With the valve 18 closed, the valves 20 and 24 were opened and the reaction products were collected in the reaction vessel 14, the filter 22, the traps 28 and 32, and the gas sampling bag 34. Note that the trap 32 was cooled by a cooler (which was capable of cooling to –80° C.) using ethanol as the cooling medium.

Example 2

Water and supercritical CO$_2$ were reacted and the reaction products were collected in the same manner as in Example 1, except that 2.0 g of catalytic particles and 1 mL of pure water were used and the pressure in the reaction vessel 14 was maintained at 8.9 MPa.

Comparative Example

The reaction between water and supercritical CO$_2$ and the collection of the reaction products were attempted in the same manner as in Example 2, except that no catalytic particles were used and the pressure in the reaction vessel 14 was maintained at 8.1 MPa.

2. Analysis

Analysis of Product from Example 1

Figure 2:
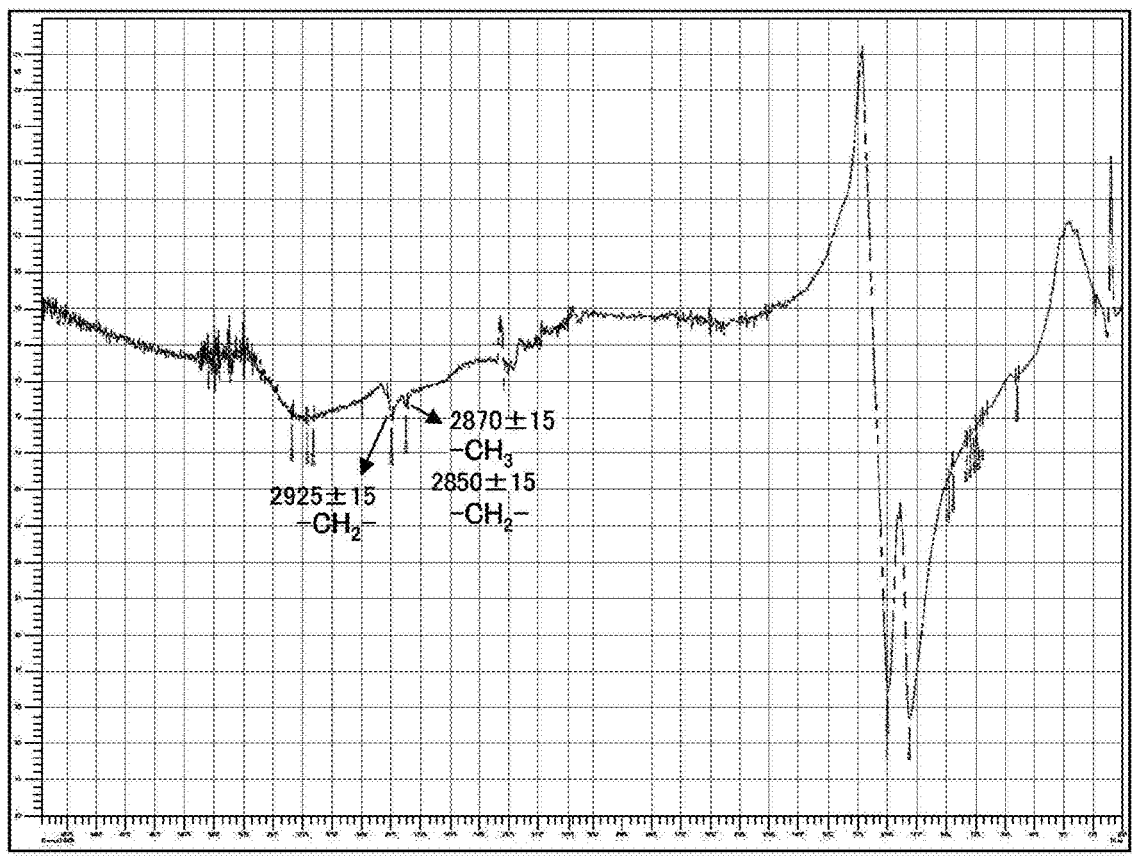
FIG. 2 A FT-IR spectrum of adherent matter on the filter from Example 1.

After the reaction in Example 1, black solids were adhered to the filter 22. The black solids were analyzed by Fourier transform infrared (FT-IR) spectroscopy using a Fourier transform infrared (FT-IR) spectrophotometer (IR Affinity-1 manufactured by Shimadzu Corporation). This FT-IR spectrum is shown in FIG. 2. As shown in FIG. 2, peaks attributed to the C—H stretching vibration of —CH$_2$— were observed at 2925±15 cm$^{-1}$ and 2850±15 cm$^{-1}$. In addition, a peak attributed to the C—H stretching vibration of —CH$_3$ was observed at 2870±15 cm$^{-1}$ These results suggest that the black solids contained a long-chain alkane hydrocarbon.

The residue in the reaction vessel 14, the adherent matter on the filter 22, and the adherent matter in the trap 32 were extracted with deuterated chloroform. These deuterated chloroform solutions, the deuterated chloroform solution in the trap 28, and the gas in the gas sampling bag 34 were analyzed by gas chromatography-mass spectrometry (GC-MS) using a gas chromatograph mass spectrometer (GC-MS) (GCMS-QP2010SE manufactured by Shimadzu Corporation). FIGS. 3 to 7 each show the chromatogram of the ion peaks detected at m/z 57.

Figure 3:
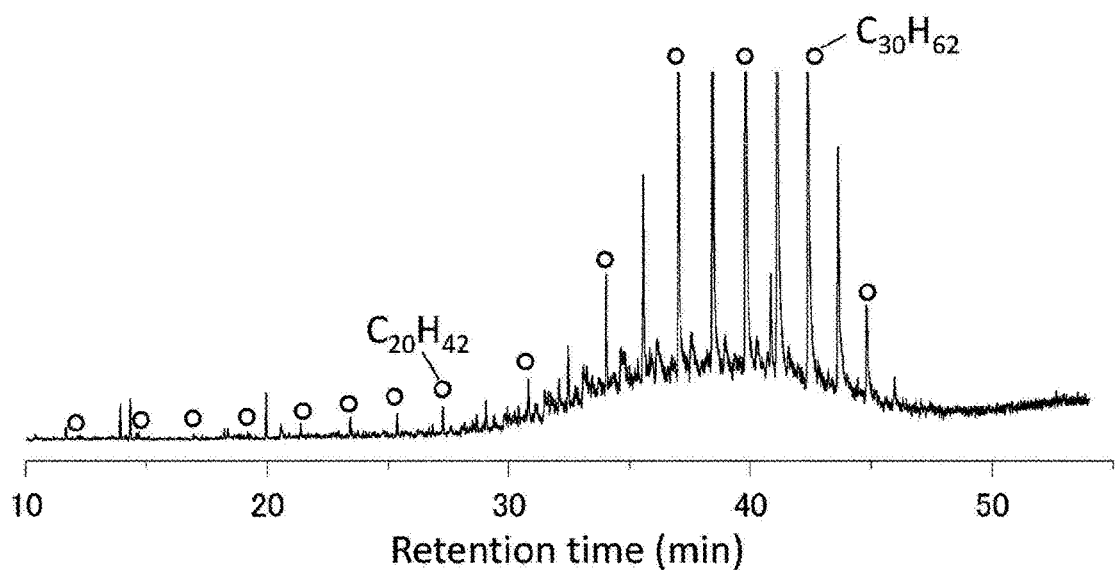
FIG. 3 A GC-MS chromatogram of residue in the reaction vessel from Example 1.
Figure 4:
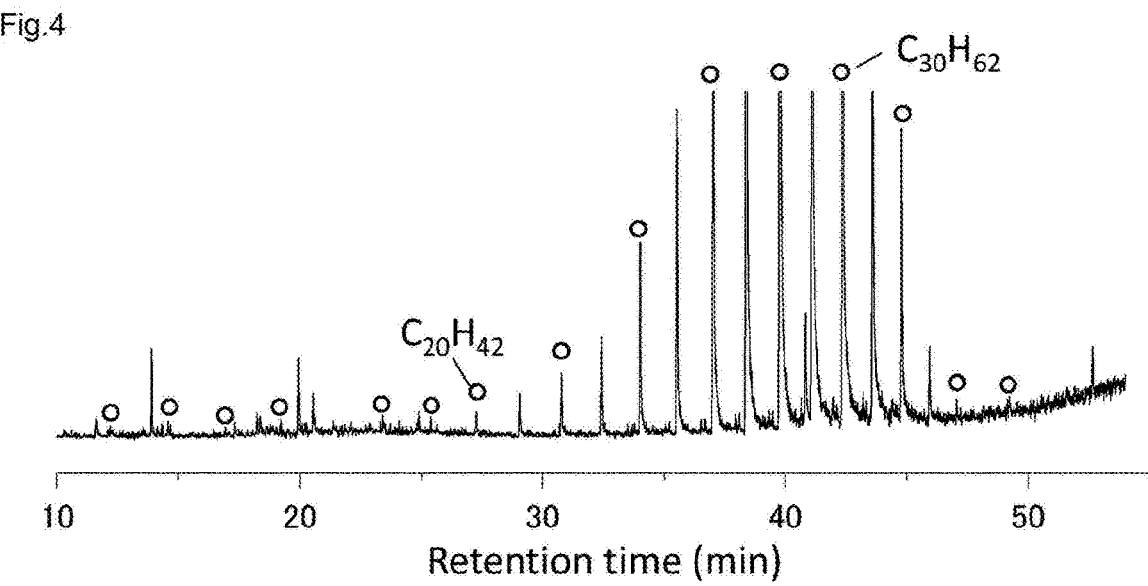
FIG. 4 A GC-MS chromatogram of adherent matter on the filter from Example 1.
Figure 5:
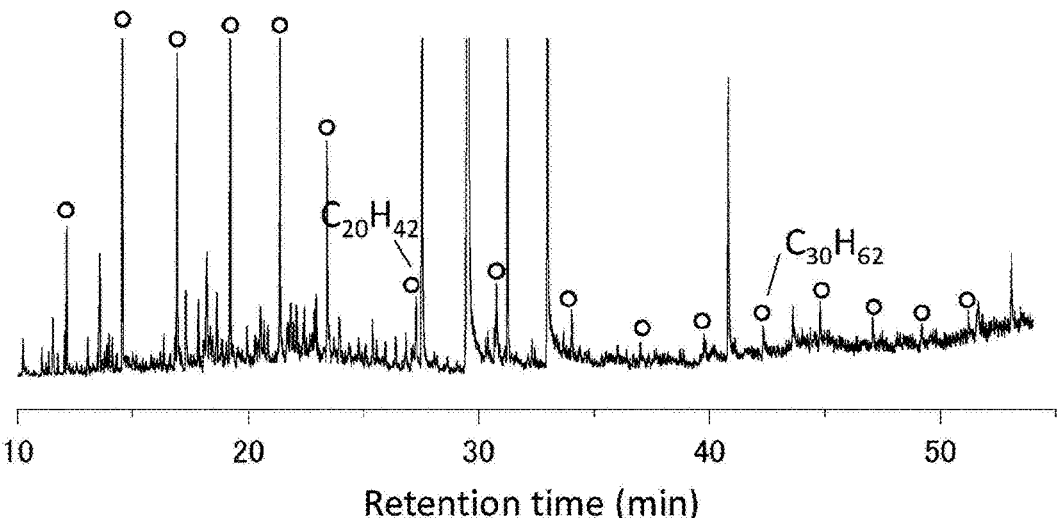
FIG. 5 A GC-MS chromatogram of a deuterated chloroform solution in the first trap of the collection unit from Example 1.
Figure 6:
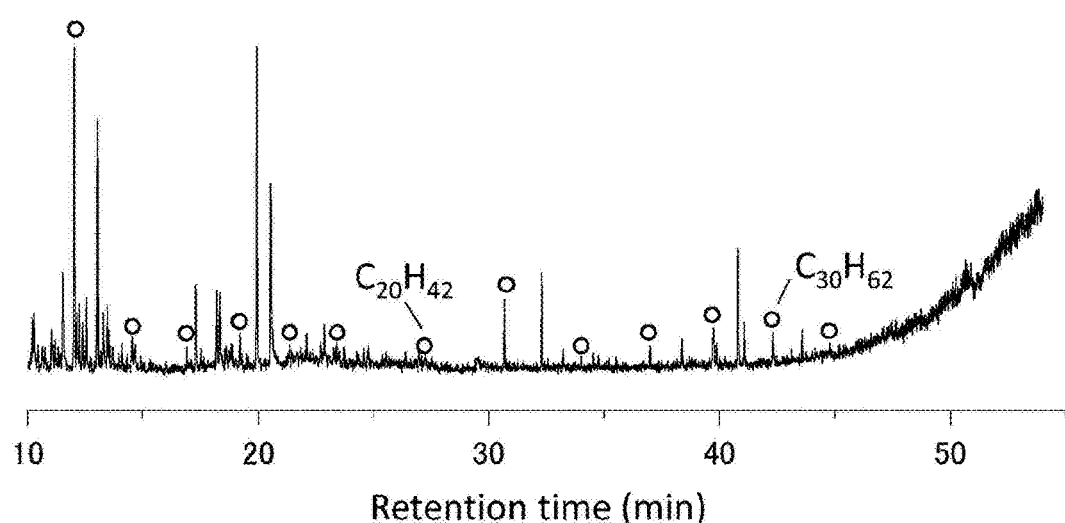
FIG. 6 A GC-MS chromatogram of adherent matter in the last trap of the collection unit from Example 1.
Figure 7:
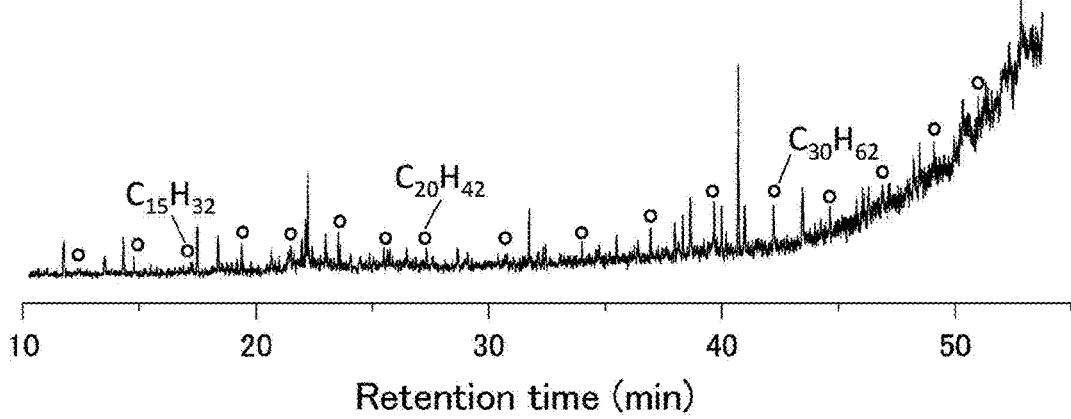
FIG. 7 A GC-MS chromatogram of gas in the gas sampling bag from Example 1.

FIG. 3 shows a chromatogram of the residue in the reaction vessel 14. FIG. 4 shows a chromatogram of the adherent matter on the filter 22. FIG. 5 shows a chromatogram of the deuterated chloroform solution in the trap 28. FIG. 6 shows a chromatogram of the adherent matter in the trap 32. FIG. 7 shows a chromatogram of the gas in the gas sampling bag 34. As shown in FIGS. 3 to 7, peaks corresponding to C$_{30}$H$_{62}$ were detected from the reaction products present at all sites. In other words, a C30-based hydrocarbon was found to be synthesized in the present example. The number of carbon atoms corresponding to the peak at each retention time is based on the GC-MS analysis peak of a standard sample, i.e., a mixture of alkanes from C$_{10}$H$_{22}$ to C$_{38}$H$_{78}$.

Figure 8:
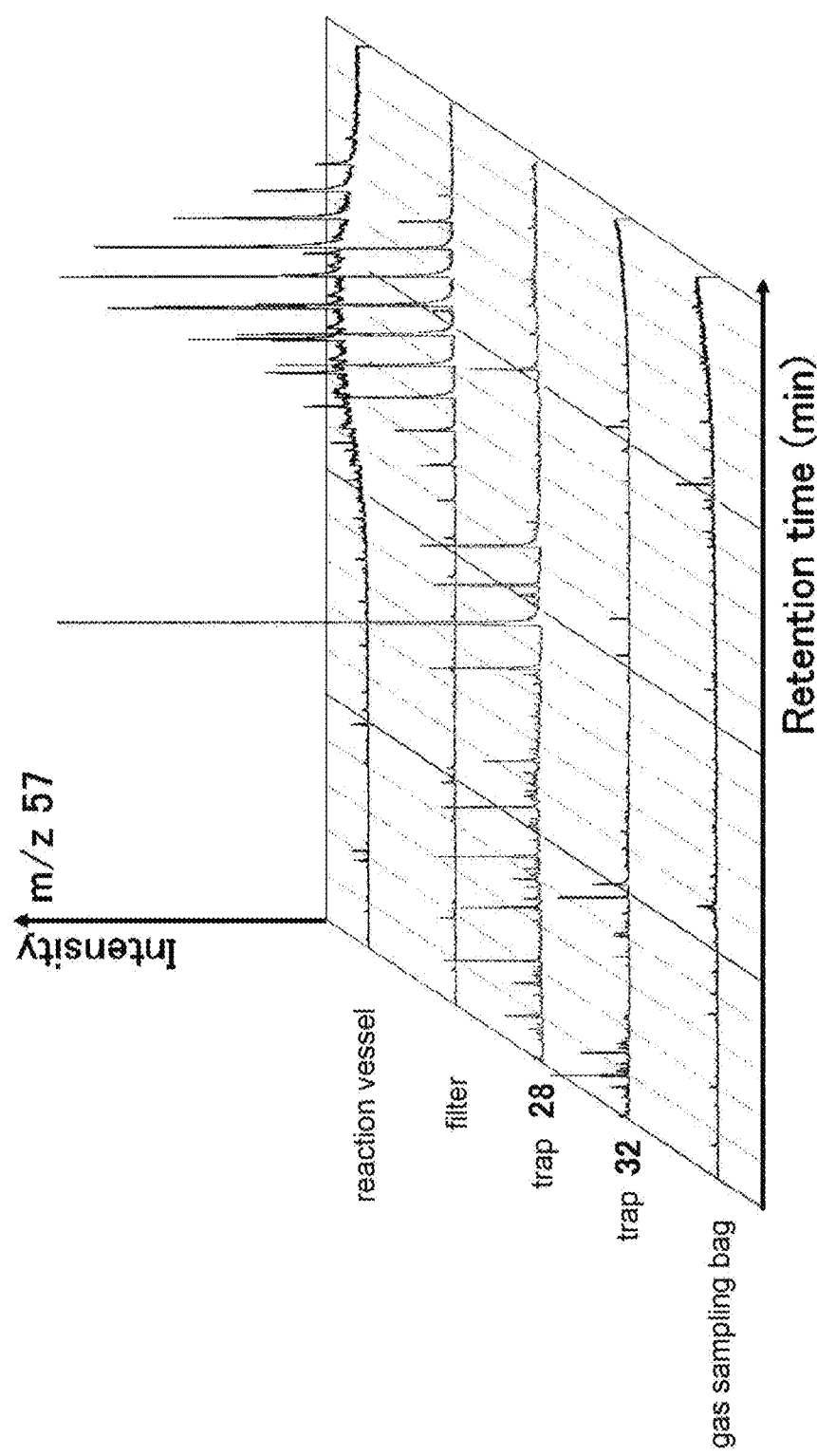
FIG. 8 GC-MS chromatograms of products at various sites of the reactor and collection unit from Example 1.

FIG. 8 shows the chromatograms of FIGS. 3 to 7 side by side. A series of long-chain alkane hydrocarbons ranging from C$_{13}$H$_{28}$ to C$_{38}$H$_{78}$ were found to be present in the gas of the reaction product. In other words, we found that a hydrocarbon can be synthesized by reacting water and supercritical CO$_2$ in the presence of a catalytic metal.

Analysis of Product from Example 2

After the reaction in Example 2, black solids were adhered to the filter 22 and inside the piping. The residue in the reaction vessel 14 and the adherent matter on the filter 22 resulting from the reaction in Example 2 were extracted with deuterated chloroform. GC-MS analyses of the deuterated chloroform solutions confirmed the presence of a C30-based hydrocarbon.

Analysis of Product from Comparative Example

Only transparent droplets were observed as the residue in the reaction vessel 14 and the matter on the filter 22. These droplets were extracted with deuterated chloroform and analyzed by GC-MS. As a result, only deuterated chloroform was detected from the residue in the reaction vessel 14 and the matter on the filter 22. In other words, we found that a hydrocarbon was not formed from water and supercritical CO$_2$ without the presence of a catalytic metal.

DESCRIPTION OF REFERENCE NUMERALS

10 Reactor
12 Collection unit
14 Reaction vessel
16 Heater
18, 20, 24 Valves
22 Filter
26 Deuterated chloroform
28, 32 Traps
Cooling means
34 Gas sampling bag
P Pressure gauge
T Thermometer

The invention claimed is:
1. A method for producing a hydrocarbon comprising:
introducing catalytic particles comprising a catalytic metal and CO$_2$ into an underground storage site where moisture is present, the pressure is 5 MPa or higher, and the temperature is 40° C. or higher, thereby bringing CO$_2$ into a subcritical or supercritical state; and
reacting water in the moisture and CO$_2$ in the subcritical or supercritical state at the storage site to synthesize the hydrocarbon.

2. The method for producing a hydrocarbon according to claim 1, wherein the catalytic particles comprises a core which is a nanoparticle support, and a shell which is the catalytic metal.

3. The method for producing a hydrocarbon according to claim 1, wherein the catalytic metal is a metal that allows the Fischer-Tropsch reaction to proceed.

4. The method for producing a hydrocarbon according to claim 1, wherein the storage site is at a point between 800 m and 1,200 m below the ground surface.

5. The method for producing a hydrocarbon according to claim 1, wherein the catalytic metal is one or more of Ni, Fe, Co, and Pd.

6. The method for producing a hydrocarbon according to claim 1, wherein the pressure at the storage site is 8 MPa or higher.

* * * * *